United States Patent [19]

Wolff et al.

[11] Patent Number: 5,641,851
[45] Date of Patent: Jun. 24, 1997

US005641851A

[54] PREPARATION OF BIURET-CONTAINING POLYISOCYANATES

[75] Inventors: Stefan Wolff, Limburgerhof; Wolfgang Heider, Neustadt; Werner Langer, Ludwigshafen; Hans Renz, Meckenheim, all of Germany

[73] Assignee: BASF Aktiengesellschaft, Germany

[21] Appl. No.: 551,213

[22] Filed: Oct. 31, 1995

[30] Foreign Application Priority Data

Dec. 9, 1994 [DE] Germany ............... 44 43 885.0

[51] Int. Cl.$^6$ ................................ C08G 18/30
[52] U.S. Cl. .............. 528/44; 252/182.2; 560/335
[58] Field of Search .............. 528/44; 252/182.2; 560/335

[56] References Cited

U.S. PATENT DOCUMENTS

| | | | |
|---|---|---|---|
| 3,350,438 | 10/1967 | Hennig | 521/162 |
| 4,028,392 | 6/1977 | Ogawa et al. | 252/182.22 |
| 4,613,686 | 9/1986 | König et al. | 560/335 |
| 4,656,223 | 4/1987 | König et al. | 524/871 |
| 4,841,059 | 6/1989 | Schriewer et al. | 546/312 |
| 4,983,762 | 1/1991 | Robin | 560/335 |
| 5,103,045 | 4/1992 | Robin et al. | 560/335 |

FOREIGN PATENT DOCUMENTS

| | | |
|---|---|---|
| 744750 | 10/1966 | Canada ............... 560/335 |
| 150769 | 8/1985 | European Pat. Off. . |
| 177059 | 4/1986 | European Pat. Off. . |
| 183150 | 6/1986 | European Pat. Off. . |
| 251952 | 1/1988 | European Pat. Off. . |
| 259233 | 3/1988 | European Pat. Off. . |
| 1174760 | 2/1963 | Germany . |
| 2918739 | 11/1980 | Germany . |

OTHER PUBLICATIONS

Chem Abstract, vol. 7, No. 201, (C–189)(1346) (Sep. 6, 1983), JP58–98377, published Jun. 11, 1983.

*Primary Examiner*—Rachel Gorr
*Attorney, Agent, or Firm*—Mary E. Golota

[57] ABSTRACT

The invention is to a process for the preparation of biuret-containing polyisocyanates by catalytic reaction of aliphatic and/or cycloaliphatic diisocyanates with a biuretizing agent, where the biuretizing agent employed is water in finely disperse form and the reaction is carried out in the presence of OH-acidic compounds.

10 Claims, No Drawings

PREPARATION OF BIURET-CONTAINING POLYISOCYANATES

BACKGROUND OF THE INVENTION

The invention relates to a process for the preparation of biuret-containing polyisocyanates by catalytic reaction of aliphatic and/or cycloaliphatic diisocyanates with a biuretizing agent, in which, in accordance with the invention, the biuretizing agent employed is water in finely disperse form and the reaction is carried out in the presence of OH-acidic compounds.

Biruet-containing aliphatic and cycloaliphatic polyisocyanates are employed, inter alia, in high-quality light- and weather-resistant two-pack polyurethane coating materials.

The preparation of polyisocyanates having a biuret structure has been known for a long time, and is customarily accomplished by reacting diisocyanates with a biuretizing agent such as, for example, water or water donors, at relatively high temperatures, and then separating off excess monomer by distillation in one or more stages.

Thus, when using water donors such as tert-butanol as biuretizing agent, with acid catalysis, water is generated in situ. For this to occur, however, high reaction temperatures of more than 140° C. are usually necessary, and at these temperatures the reaction products undergo a yellow discoloration. For reasons connected with their performance, for example as clearcoats, however, it is desired that the products be colorless as far as possible. Furthermore, the use of a water-donating and generally OH-containing biuretizing agent promote the formation of by-products which are devoid of biuret structure. These by-products may likewise have effects which are adverse in terms of performance properties, or may impair the stability of the product on storage, or give rise to process-related problems.

For this reason, the use of water as a biuretizing agent would be ideal. The use of water without additives, however, gives rise to two grave disadvantages:
1. The formation of insoluble polyureas in the reaction cannot in general be avoided.
2. The products obained have a poor stability on storage with respect to breakdown to the monomer, thereby rapidly exceeding the 0.5% limit value (the inclusion of which on the label is mandatory), especially in the course of storage at above room temperature.

Attempts have been made to circumvent these problems by a modified procedure. The patent literature contains a multiplicity of variant methods for the preparation of polyisocyanates with biuret structure which employ water as biuretizing agent.

For example, U.S. Pat. No. 4,028,392 has already described the reaction of isocyanates with water in the presence of hydrophilic organic solvents such as, for example, trialkyl phosphates and ethylene glycol monomethyl acetate. According to EP-B-259 233, the reaction is carried out in the presence of at least one carboxylic acid and/or one carboxylic anhydride. Also envisaged is the concomitant use of methyl and/or ethyl esters of phosphoric acid, and of alkoxyalkyl carboxylates, as solubilizers. A disadvantage in this context is that the use of a solvent or solvent mixture in the necessary quantities results in a lower space-time yield of polyisocyanate being achieved than is the case without the use of solvent. In addition, a more complex distillation is necessary, possibly with the separation of solvent.

In EP-B-251 952, organic polyisocyanates with biuret structure are prepared from diisocyanates and water under a total pressure of at least 1.2 bar, at a partial pressure of carbon dioxide of at least 0.2 bar. However, this mode of operation using carbon dioxide at elevated pressure necessitates specific conditions and is therefore very complex to manage.

DE-C-29 18 739 describes a process for the preparation of polyisocyanates with biuret structure by reacting hexamethylene diisocyanate (HDI) with water, in which process the water is supplied in the form of vapor in a mixture with air and/or an inert gas, which mixture has a moisture content of from 0.1 to 2.0 kg/kg, to a reaction mixture which is maintained at from 110° to 130 C., and reaction is carried out at from 150° to 170° C. The disadvantage here is that numerous insoluble polyureas are formed in the course of this reaction. This may lead to the clogging of plant components, especially lines.

SUMMARY OF THE INVENTION

It is an object of the present invention to develop a process which solves the problems of the known processes in the preparation of biuret-conaining isocyanates. The intention is in particular to, as far as possible, avoid the formation of polyurea, and to ensure good storage stability with respect to the breakdown of residual monomers, and to obtain oligobiurets which are as far as possible colorless.

We have found that this object is achieved, in accordance with the invention, by employing water in finely disperse form as biuretizing agent and carrying out the reaction in the presence of OH-acidic compounds.

The present invention therefore relates to a process for the preparation of biuret-containing polyisocyanates by catalytic reaction of aliphatic and/or cycloaliphatic diisocyanates with a biuretizing agent, which comprises employing water in finely disperse form as biuretizing agent and carrying out the reaction in the presence of OH-acidic compounds.

The biuret-containing polyisocyanates prepared in this way are virtually colorless and have a low residual monomer content which rises only slowly, even at storage temperatures above room temperature, and therefore also satisfies the requirements of workplace safety under these conditions. These polyisocyanates are employed in particular in one-pack or two-pack polyurethane coating materials, adhesives and polyurethane dispersions.

Suitable starting materials for preparing the biuret-containing polyisocyanates are the aliphatic and/or cycloaliphatic diisocyanates which are known per se, alone or in mixtures with one another, examples being alkylene diisocyanates having 4 to 12 carbon atoms in the alkylene radical, 1,12-dodecane diisocyanate 2-ethyltetramethylene 1,4-diisocyanate, 2-methylpentamethylene 1,5-diisocyanate, tetramethylene 1,4-diisocyanate and hexamethylene 1,6-diisocyanate (HDI); cycloaliphatic diisocyanates, such as cyclohexane 1,3- and 1,4-diisocyanate, and any desired mixtures of these isomers. Preference is given to employing 2-butyl-2-ethylpentamethylene diisocyanate, 2-methylpentamethylene diisocyanate, isophorone diisocyanate (IPDI) and HDI. Particular preference is given to HDI prepared without phosgene.

The biuretizing agent used is water in finely disperse form. This fine dispersion can be brought about by the use of known, suitable apparatus and reactors incorporating a stirrer mechanism. In order to introduce water into the diisocyanate in the most finely disperse form possible, the water is preferably employed in the form of steam.

If the flow of steam is diluted by an inert gas, the process can be monitored and controlled with greater facility. As inert gas, preference is given in accordance with the invention to nitrogen and/or carbon dioxide. The steam can be diluted by inert gas such that from 10 to 95% by volume of inert gas is present in the gas stream.

In order to attain the desired properties, such as the required stability of the products on storage, the biuretization of the diisocyanates is carried out, in accordance with the invention, by bringing water or steam in finely disperse form into conjunction with OH-acidic compounds. The use of OH-acidic compounds accelerates biuret formation and reduces the formation of unwanted byproducts.

In accordance with the invention, particularly suitable OH-acidic compounds are protonic acids. Examples which can be employed and which have proven particularly suitable are: phosphoric acids and/or their mono- and/or dialkyl (aryl) esters and/or hydrogen sulfates. Preference is given to the use of mono- and/or dialkyl(aryl) esters of phosphoric acid whose aliphatic, branched aliphatic, araliphatic or aromatic radicals carry from 1 to 30, preferably from 4 to 20, carbon atoms. Examples which find application are di(2-ethylhexyl) phosphate and dihexadecyl phosphate. Particularly suitable hydrogen sulfates are tetralkylammonium hydrogen sulfates whose aliphatic, branched aliphatic or araliphatic radicals carry from 1 to 30, preferably from 4 to 20, carbon atoms. Particularly suitable are dibutyl phosphate and diisopropyl phosphate. Di(2-ethylhexyl) phosphate is preferred. The (ar)aliphatic carboxylic acids described, for example, in EP-A-259 233 have proven to be less effective.

The OH-acidic compounds to be employed in accordance with the invention have the advantage that they are of low volatility and therefore, in the form of salts if desired, can be filtered off from the product mixture or remain in the end product as non-disrupting compounds, or else they form, during the reaction, decomposition products or by-products which are likewise non-disrupting. A further advantage is the good catalytic activity of the acids.

These OH-acidic compounds are expediently employed in quantities of from 0.01 to 2 mol%, preferably from 0.1 to 2.5 mol%, based on the diisocyanate employed.

In order to suppress the formation of insoluble polyureas to even better extent, it is possible in addition to use solvents as solubilizers. Examples of solvents suitable for this purpose are alkoxyalkyl carboxylates and/or trialkyl phosphates. In accordance with the invention, preference is given to employing methoxypropyl acetate, trimethyl phosphate and triethyl phosphate or any desired mixtures of these compounds.

The reaction of the diisocyanate with the biuretizing agent is carried out at from 60° to 200° C., preferably from 100° to 150° C.

The invention is illustrated by the following Examples.

Examples 1 to 5—According to the Invention (see Table 1)

500 g of HDI (2.97 mol) were placed in a stirred flask equipped with reflux condenser, glass tube with frit and stirrer. The glass tube with frit was connected to an apparatus for the generation of steam (a heated round-bottom flask with dropping funnel, from which water can slowly be metered into the hot flask) and a nitrogen inlet.

The nature and quantity of OH-acidic compounds (mol % based on HDI) as indicated in the Table was added to the HDI, and the mixture was preheated to 130° C. while bubbling nitrogen through it. Subsequently, steam diluted with nitrogen (20 l/h) was passed in via the glass frit, and the course of the reaction was monitored by the decrease in the NCO content. At an NCO content of 40–43%, the supply of steam was shut off (after about 60–75 min) and stirring of the reaction mixture was continued for a further 30 min under nitrogen at 130° C. Excess HDI was then separated off by distillation in a thin-film evaporator. The clear and virtually colorless bottom product obtained had a low content of residual HDI, and was then stored at 50° C. in a drying oven, and the increase in residual monomer was measured after 6 weeks (see Table 1).

Example 6—Comparison (see Table 1)

The procedure of Examples 1 to 5 was repeated but without the addition of OH-acidic compounds. The reaction was markedly slower, and, depending on the input of steam per unit time, greater or lesser quantities of insoluble polyureas were formed in the reaction mixture (0.01–0.5% by weight of polyurea based on the HDI employed).

Examples 7 and 8—According to the Invention (see Table 2)

500 g of HDI (2.97 mol), 250 g of triethyl phosphate and the stated quantity of the particular OH-acidic compound (mol % based on HDI) were placed in a stirred flask fitted with reflux condenser and stirrer, and the mixture was preheated to 130° C. 6.4 g of water were then added dropwise with vigorous stirring under a nitrogen atmosphere. The mixture reacted at 130° C., accompanied by vigorous evolution of $CO_2$, over the course of 3 hours, to give a NCO content of 40–42% (calculated back to the solvent-free mixture). After this, excess HDI and solvent were separated off by distillation in a thin-film evaporator. The clear and virtually colorless bottom product obtained, having a low content of residual HDI, was then stored in a drying oven at 50° C., and the increase in residual monomer was measured after 6 weeks.

Example 9—Comparison (see Table 2)

The procedure of Examples 7 and 8 was repeated but without the addition of OH-acidic compounds. The reaction was markedly slower, and insoluble ureas formed in the gas space above the reactants, the ureas becoming deposited at unheated sites on the reaction apparatus.

TABLE 1

Preparation of HDI-biuret with water vapor

| Experiment | OH-acidic compounds [mol %] | NCO content [%] | Residual HDI content [%] immediately after | Residual HDI content [%] 42 days at 50° C. | Product color number [Apha] |
|---|---|---|---|---|---|
| 1 | Di(2-ethylhexyl) phosphate [0.1] | 23.3 | 0.16 | 0.3 | <10 |
| 2 | Di(2-ethylhexyl) phosphate [0.2] | 23.3 | 0.15 | 0.21 | <10 |
| 3 | di(2-ethylhexyl) phosphate [0.4] | 22.9 | 0.24 | 0.26 | <10 |
| 4 | Dihexadecyl phosphate [0.2] | 23.1 | 0.19 | 0.3 | <10 |
| 5 | Dihexadecyl phosphate [0.46] | 22.8 | 0.12 | 0.29 | <10 |
| 6 | without OH-acidic compounds | 22 | 0.25 | 1.65 | 10–20 |

TABLE 2

Biuretization of HDI with water in triethyl phosphate

| Experiment | OH-acidic compounds [mol %] | NCO content [%] | Residual HDI content [%] immediately after | Residual HDI content [%] 42 days at 50° C. | Product color number [Apha] |
|---|---|---|---|---|---|
| 7 | Di(2-ethylhexyl) phosphate [0.1] | 23.3 | 0.13 | 0.30 | <10 |
| 8 | Di(2-ethylhexyl) phosphate [0.2] | 23.3 | 0.18 | 0.29 | <10 |
| 9 | without OH-acidic compounds | 22.6 | 0.27 | 1.6 | 10–20 |

We claim:

1. A process for the preparation of biuret-containing polyisocyanates by catalytic reaction of aliphatic and/or cycloaliphatic diisocyanates with a biuretizing agent, which comprises employing water in the form of steam as biuretizing agent and carrying out the reaction in the presence of OH-acidic compounds, selected from the group consisting of phosphoric acid and/or their mono- and/or dialkyl(aryl) esters and/or hydrogen sulfates.

2. A process as claimed in claim 1, wherein, the biuretizing agent employed is steam in conjunction with an inert gas.

3. A process as claimed in claim 1, wherein the OH-acidic compounds employed are tetraalkylammonium hydrogen sulfates.

4. A process as claimed in claim 1, wherein, in addition, methoxypropyl acetate and/or trimethyl phosphate and/or triethyl phosphate are employed as solubilizers.

5. A process as claimed in claim 2, wherein, in addition, methoxypropyl acetate and/or trimethyl phosphate and/or triethyl phosphate are employed as solubilizers.

6. A process as claimed in claim 3, wherein, in addition, methoxypropyl acetate and/or trimethyl phosphate and/or triethyl phosphate are employed as solubilizers.

7. A process as claimed in claim 1, wherein the diisocyanate used is hexamethylene diisocyanate.

8. A process as claimed in claim 2, wherein the diisocyanate used is hexamethylene diisocyanate.

9. A process as claimed in claim 3, wherein the diisocyanate used is hexamethylene diisocyanate.

10. A process as claimed in any one of claims 1, or 2, wherein the diisocyanate employed is isophorone diisocyanate.

* * * * *